(12) United States Patent
Kim et al.

(10) Patent No.: US 12,667,639 B2
(45) Date of Patent: Jun. 30, 2026

(54) FRAGRANCE GENERATOR FOR VEHICLE

(71) Applicant: Hanon Systems, Daejeon (KR)

(72) Inventors: Jae Ho Kim, Daejeon (KR); Ji-Yong Park, Daejeon (KR); Su Jin Woo, Daejeon (KR)

(73) Assignee: HANON SYSTEMS, Daejeon (KR)

( * ) Notice: Subject to any disclaimer, the term of this patent is extended or adjusted under 35 U.S.C. 154(b) by 262 days.

(21) Appl. No.: 18/035,169

(22) PCT Filed: Nov. 25, 2021

(86) PCT No.: PCT/KR2021/017490
§ 371 (c)(1),
(2) Date: May 3, 2023

(87) PCT Pub. No.: WO2022/119233
PCT Pub. Date: Jun. 9, 2022

(65) Prior Publication Data
US 2023/0405172 A1      Dec. 21, 2023

(30) Foreign Application Priority Data
Dec. 4, 2020    (KR) ........................ 10-2020-0168906

(51) Int. Cl.
*A61L 9/12* (2006.01)
*B60H 3/00* (2006.01)

(52) U.S. Cl.
CPC ............ *A61L 9/125* (2013.01); *B60H 3/0035* (2013.01); *A61L 2209/133* (2013.01)

(58) Field of Classification Search
CPC .. A61L 9/125; A61L 2209/133; B60H 3/0035
USPC ........................................................... 239/58
See application file for complete search history.

(56) References Cited

U.S. PATENT DOCUMENTS

| | | | | |
|---|---|---|---|---|
| 7,712,683 | B2 * | 5/2010 | Robert ...................... | B05B 7/30 |
| | | | | 261/78.2 |
| 12,011,519 | B2 * | 6/2024 | Sward ...................... | A61L 9/14 |
| 2019/0077228 | A1 | 3/2019 | Goto | |
| 2024/0253425 | A1 * | 8/2024 | Otsuka ................. | B60H 3/0035 |

FOREIGN PATENT DOCUMENTS

| | | | |
|---|---|---|---|
| JP | 2010179786 A | 8/2010 | |
| KR | 200239958 Y1 | 11/2001 | |
| KR | 100381749 B1 | 4/2003 | |

(Continued)

*Primary Examiner* — Chee-Chong Lee
(74) *Attorney, Agent, or Firm* — NORTON ROSE FULBRIGHT US LLP

(57) ABSTRACT

The present invention relates to a fragrance generator for a vehicle, the fragrance generator including a storage casing configured to accommodate a plurality of fragrance cartridges therein, a cover casing coupled to one surface of the storage casing and configured to discharge a fragrance discharged from the fragrance cartridge, and a rotary member interposed between the storage casing and the cover casing and having a length extending in two directions of one surface, in which one or both of a pair of lateral casings disposed on two opposite surfaces of the storage casing is separably coupled to the storage casing, thereby further improving assembling performance and durability.

14 Claims, 11 Drawing Sheets

(56)                 References Cited

FOREIGN PATENT DOCUMENTS

| | | | |
|---|---|---|---|
| KR | 200358419 | Y1 | 8/2004 |
| KR | 200394008 | Y1 | 8/2005 |
| KR | 10-1313331 | B1 | 9/2013 |
| KR | 101353427 | B1 | 1/2014 |
| KR | 10-1760305 | B1 | 7/2017 |

* cited by examiner (a)

(b)

FRAGRANCE GENERATOR FOR VEHICLE

CROSS REFERENCE TO RELATED APPLICATIONS

This application is a national phase under 35 U.S.C. § 371 of International Application No. PCT/KR2021/017490 filed on Nov. 25, 2021, which claims the benefit of priority from Korean Patent Application No. 10-2020-0168906 filed on Dec. 4, 2020. The entire contents of these applications are incorporated herein by reference in their entirety.

TECHNICAL FIELD

The present invention relates to a fragrance generator for a vehicle, and more particularly, to a fragrance generator for a vehicle, which is capable of supplying a vehicle interior with fragrance components stored in a plurality of cartridges.

BACKGROUND ART

An air conditioning device for a vehicle refers to a device for heating or cooling a vehicle interior by heating or cooling air during a process of introducing air existing outside a vehicle into the vehicle interior or circulating air in the vehicle interior. Further, the air conditioning device for a vehicle includes a blower unit, an evaporator, a heater core, and the like and is configured to blow air into the vehicle interior.

In this case, in case that the air conditioning device for a vehicle operates, there occurs a problem in that harmful substances, such as dust, soot, and smoke gas, which are introduced from the outside of the vehicle interior, and bacterial foreign substances, which exist in a flow path in the air conditioning device, are introduced into the vehicle interior. Therefore, in the related art, a fragrance generator connected to the air conditioning device is installed in the vehicle to purify air in the vehicle and remove offensive odor.

The fragrance generators in the related art are classified into a fragrance generator, which uses a solid and volatilizes the solid, and a fragrance generator which uses a liquid and volatilizes or sprays the liquid. However, there is a limitation in that the fragrance generator inevitably performs only a particular one function or discharges only a single type of fragrance. Therefore, Japanese Patent Application Laid-Open No. 2010-179786 (entitled "Air Freshening Device for Vehicle" published on Aug. 19, 2010) discloses an air freshening device capable of discharging two fragrances. Korean Patent No. 10-1313331 (entitled "Multi-Fragrance Supply Device for Vehicle" published on Sep. 27, 2013) and Korean Patent No. 10-1760305 (entitled "Fragrance Extraction Device for Vehicle published on Jul. 24, 2017) disclose fragrance generators capable of mixing a plurality of fragrances or selectively discharging a plurality of fragrances.

The fragrance generators in the related art have excellent air freshening performance. However, performance in assembling internal components is low, which causes a problem in that an excessive amount of time is required to assemble the fragrance generator, or the fragrance generator is erroneously assembled because of an operator's mistake, and a fluid in the fragrance generator leaks. Further, in case that a casing is integrally produced to improve assembling performance, there is a problem in that the entire casing needs to be replaced even when the casing is partially damaged, which makes it difficult to perform maintenance.

DOCUMENTS OF RELATED ART

Patent Documents

JP 2010-179786 A (published on Aug. 19, 2010)
KR 10-1313331 B1 (published on Sep. 27, 2013)
KR 10-1353427 B1 (published on Jan. 23, 2014)
KR 10-1760305 B1 (published on Jul. 24, 2017)

DISCLOSURE

Technical Problem

The present invention has been made in an effort to solve the above-mentioned problem, and an object of the present invention is to provide a fragrance generator for a vehicle, in which a storage casing and a lateral casing may be coupled to define a housing part, which makes it possible to further improve assembling performance, and a rotary shaft of a rotary member and a rotary shaft of an opening/closing member may be fixed to the lateral casing, which makes it possible to improve durability.

Technical Solution

To achieve the above-mentioned object, the present invention provides a fragrance generator for a vehicle, the fragrance generator including: a storage casing configured to accommodate a plurality of fragrance cartridges therein; a cover casing coupled to one surface of the storage casing and configured to discharge a fragrance discharged from the fragrance cartridge; and a rotary member interposed between the storage casing and the cover casing and having a length extending in two directions of one surface, in which when the rotary member rotates, the fragrance is discharged from one or more fragrance cartridges among the plurality of fragrance cartridges and discharged through the cover casing, and in which one or both of a pair of lateral casings disposed on two opposite surfaces of the storage casing is separably coupled to the storage casing.

In addition, the fragrance generator for a vehicle according to the present invention may further include: first and second discharge ports disposed in the storage casing and respectively connected to a pair of fragrance cartridges; and an opening/closing member configured to open or close the first and second discharge ports, in which the lateral casing fixes a part of the opening/closing member.

In addition, the rotary member may include: a shaft body disposed on one surface of the storage casing and extending to two opposite sides; a power application part configured to transmit power, which is applied from an actuator, to one end of the shaft body; and an opening/closing adjustment part disposed on the shaft body and configured to control a posture of the opening/closing member, and the lateral casing may include a shaft support part into which the other end of the shaft body is inserted.

In addition, one of the pair of lateral casings may include the shaft support part, and the other lateral casing may include a shaft seating part on which one end of the shaft body is seated.

In addition, the opening/closing member may include: first and second opening/closing parts configured to respectively open or close the first and second discharge ports while rotating within a predetermined angle; and a rotary shaft connected to the first and second opening/closing parts, and the lateral casing may fix an end of the rotary shaft.

In addition, the cover casing may include: a cover body having a discharge port through which the fragrance is discharged; and a rotation stopper disposed on one side surface of the cover body, the rotary member may include: a shaft body having a length extending to two opposite sides; and a rotation adjustment part protruding from one side of the shaft body toward the cover casing and disposed on the rotation stopper, and the shaft body may rotate within a predetermined angle.

In addition, the fragrance generator for a vehicle according to the present invention may further include: a sealing member interposed between the storage casing and the cover casing, in which a coupling guide is provided on a surface, on which the storage casing and the sealing member adjoin each other, to fix a coupling position of the sealing member.

In addition, the fragrance generator for a vehicle according to the present invention may further include: a partition wall part disposed in the storage casing and configured to divide and partition an interior of the storage casing, in which the partition wall part and the sealing member are in surface contact with each other, and in which a coupling guide is provided on a surface, on which the partition wall part and the sealing member adjoin each other, to fix a coupling position of the sealing member.

In addition, the fragrance generator for a vehicle according to the present invention may further include: an opening/closing member having first and second opening/closing parts that rotate about a rotary shaft and adjust the fragrance discharged from a pair of fragrance cartridges, in which the sealing member has a groove in which a part of the rotary shaft is seated.

In addition, the cover casing and the sealing member may have insertion portions formed in surfaces of the cover casing and the sealing member that adjoin each other, such that the cover casing and the sealing member are inserted and coupled into each other.

In addition, the lateral casing may include: a lateral body; and a communication hole formed through the lateral body, and a fastening member may penetrate the communication hole and be coupled to the storage casing.

In addition, the lateral casing may include: a lateral body; and an insertion guide configured to guide coupling positions of the lateral body and one surface of the storage casing.

In addition, a mounting groove may be recessed in one surface of the storage casing so that the lateral body is inserted into the mounting groove.

In addition, the fragrance generator for a vehicle according to the present invention may further include: an opening/closing member having first and second opening/closing parts that rotate about a rotary shaft and adjust the fragrance discharged from a pair of fragrance cartridges; and an end support part configured to fix an end of the rotary shaft of the opening/closing member, in which the end support part is disposed in the lateral casing or the storage casing.

In addition, the fragrance generator for a vehicle according to the present invention may further include: a sealing member interposed between the storage casing and the cover casing, in which a part of the sealing member is disposed in the storage casing so that the rotary shaft of the opening/closing member is seated on the sealing member, and in which the rotary shaft fixed by the end support part presses one surface of the opening/closing member so that the other surface of the opening/closing member is in close contact with the sealing member in a direction in which the storage casing is disposed.

In addition, the end support part, which is disposed in the storage casing, may protrude and be inserted and coupled into a groove formed at an end of the rotary shaft, such that the protruding end support part prevents separation of the sealing member.

Advantageous Effects

According to the fragrance generator for a vehicle according to the present invention configured as described above, the storage casing and the lateral casing of the housing part are separably coupled to each other, which makes it possible to further improve the assembling performance, and the end of the rotary member or the opening/closing member is fixed to the lateral casing, which makes it possible to further improve durability.

Further, according to the fragrance generator for a vehicle according to the present invention, the configuration capable of guiding coupling is disposed between the storage casing and the sealing member, between the cover casing and the sealing member, or between the storage casing and the lateral body, which makes it possible to prevent the erroneous assembly caused by the operator's error, further reduce the assembly time, and maintain sealability.

Further, according to the fragrance generator for a vehicle according to the present invention, the rotation angle of the rotary member may be limited within a predetermined range by the rotation stopper of the cover casing, which makes it possible to prevent damage and provide a foundation for more precise control.

MODE FOR INVENTION

Hereinafter, a fragrance generator for a vehicle according to the present invention configured as described above will be described in detail with reference to the accompanying drawings.

Figure 1:
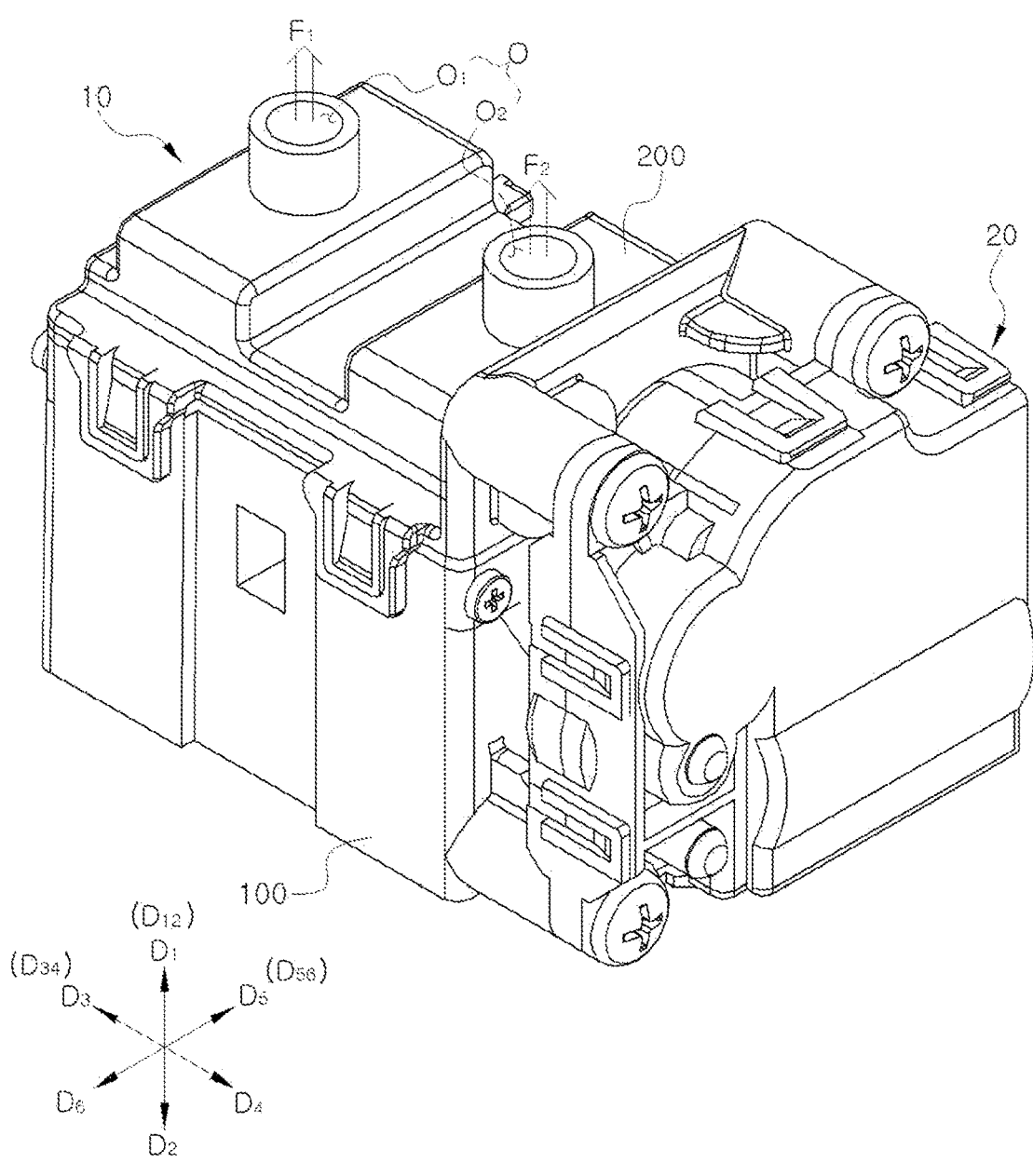
FIG. 1 is a perspective view of a fragrance generator for a vehicle according to the present invention.
Figure 2:
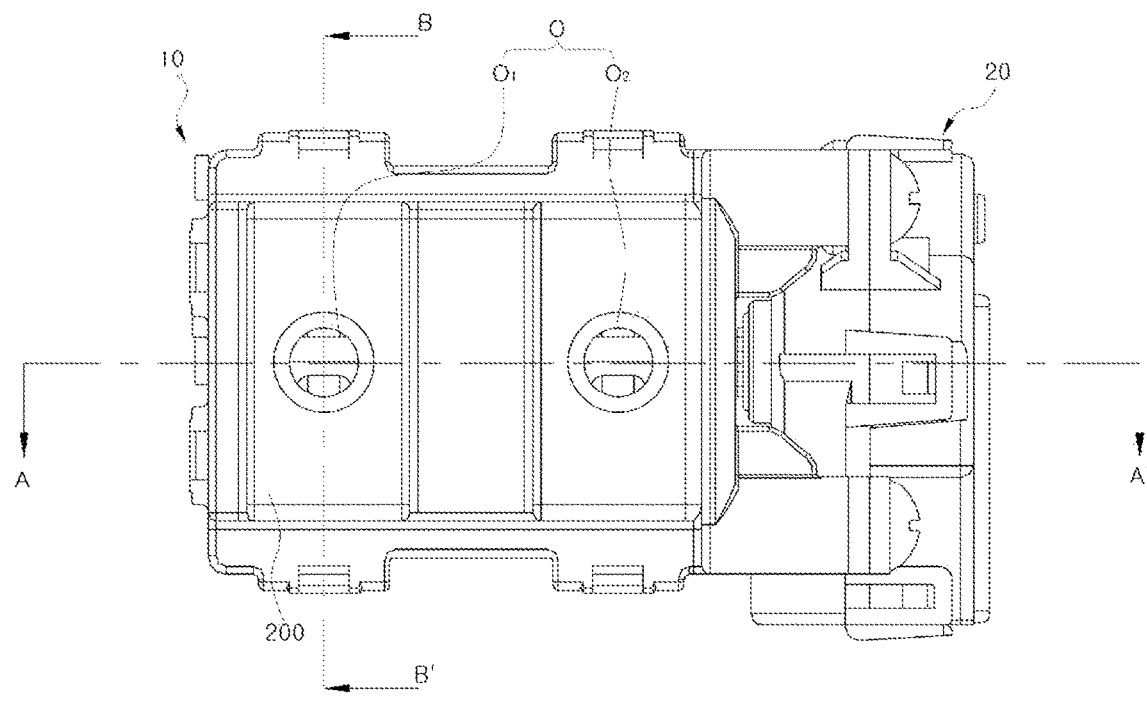
FIG. 2 is a top plan view of the fragrance generator for a vehicle according to the present invention.

FIGS. 1 and 2 relate to the fragrance generator for a vehicle according to the present invention. FIG. 1 is a perspective view of the fragrance generator for a vehicle, and FIG. 2 is a top plan view of the fragrance generator for a vehicle.

With reference to FIGS. 1 and 2, a fragrance generator 10 for a vehicle according to the present invention may be coupled to an actuator 20 and discharge a fragrance, which is generated in the fragrance generator 10, to the outside by receiving power. The fragrance generator 10 may include one or more discharge ports O. In this case, the discharge port O may be provided as a plurality of discharge ports O including a first discharge port $O_1$ and a second discharge port $O_2$. Various types of fragrances may be discharged from one discharge port O. In this case, the present invention will be described with reference to an example in which the plurality of discharge ports O including the first discharge port $O_1$ and the second discharge port $O_2$ is spaced apart from one another in two directions and discharges a first fluid $F_1$, a second fluid $F_2$, and the like. The first fluid $F_1$ and the second fluid $F_2$ may also be made of the same component or be different fragrances.

The fragrance generator 10 for a vehicle according to the present invention may include a housing part 100 configured to accommodate cartridges therein, and a cover casing 200 coupled to the housing part 100 and having the discharge ports O. Hereinafter, to more clearly describe the following contents, in FIG. 1, an upward direction is defined as an upward direction $D_1$, a direction opposite to the upward direction is defined as a downward direction $D_2$, and the upward and downward directions are defined as an upward/downward direction $D_{12}$. In addition, in FIG. 1, a leftward/upward direction is defined as a leftward direction $D_3$, a direction opposite to the leftward direction is defined as a rightward direction $D_4$, and the leftward and rightward directions are defined as a leftward/rightward direction $D_{34}$. Further, in FIG. 1, a rightward/upward direction is defined as a forward direction $D_5$, a direction opposite to the forward direction is defined as a rearward direction $D_6$, and the forward and rearward directions are defined as a forward/rearward direction $D_{56}$.

Figure 3:
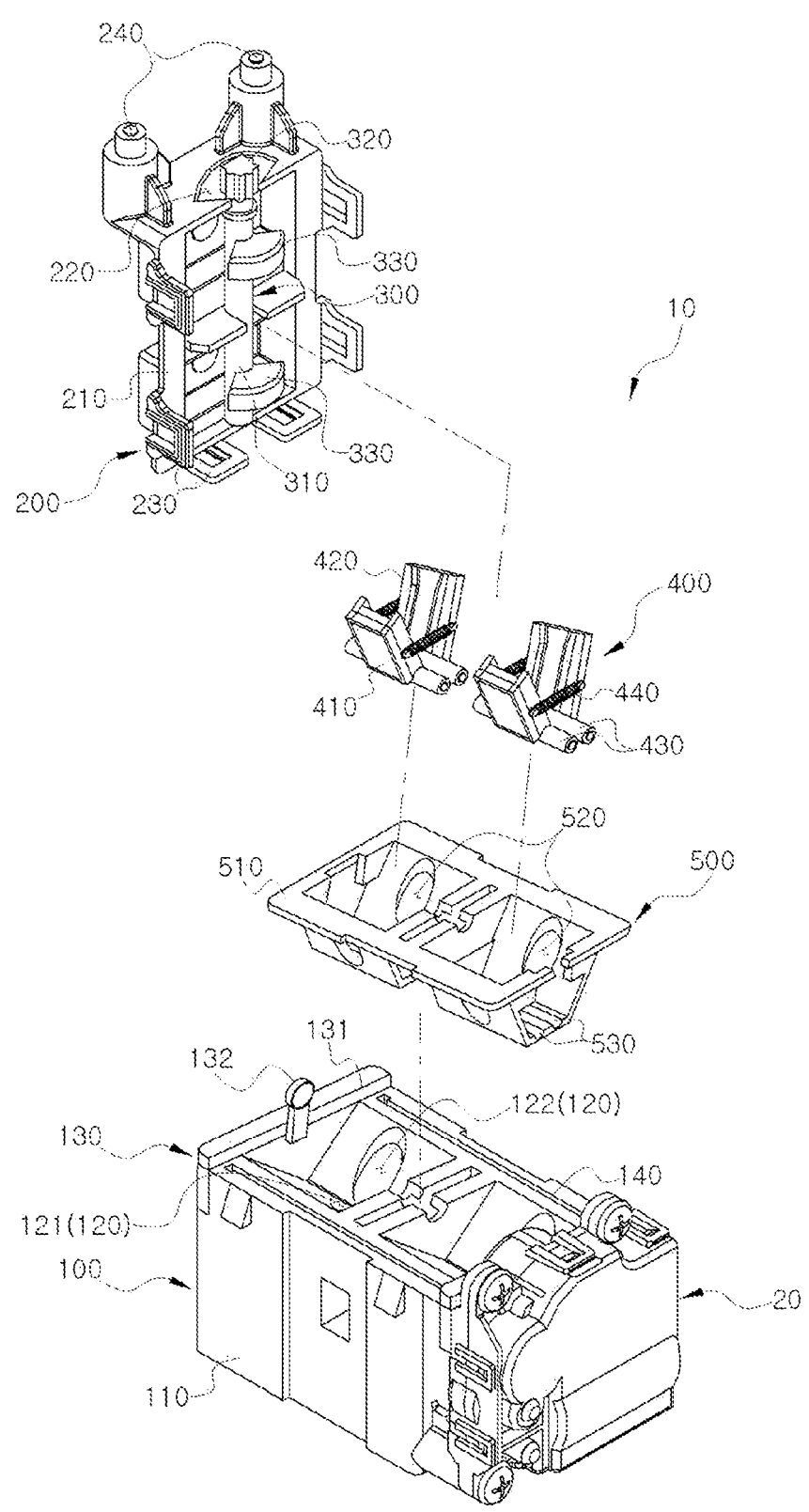
FIG. 3 is an exploded perspective view of the fragrance generator for a vehicle according to the present invention.
Figure 4:
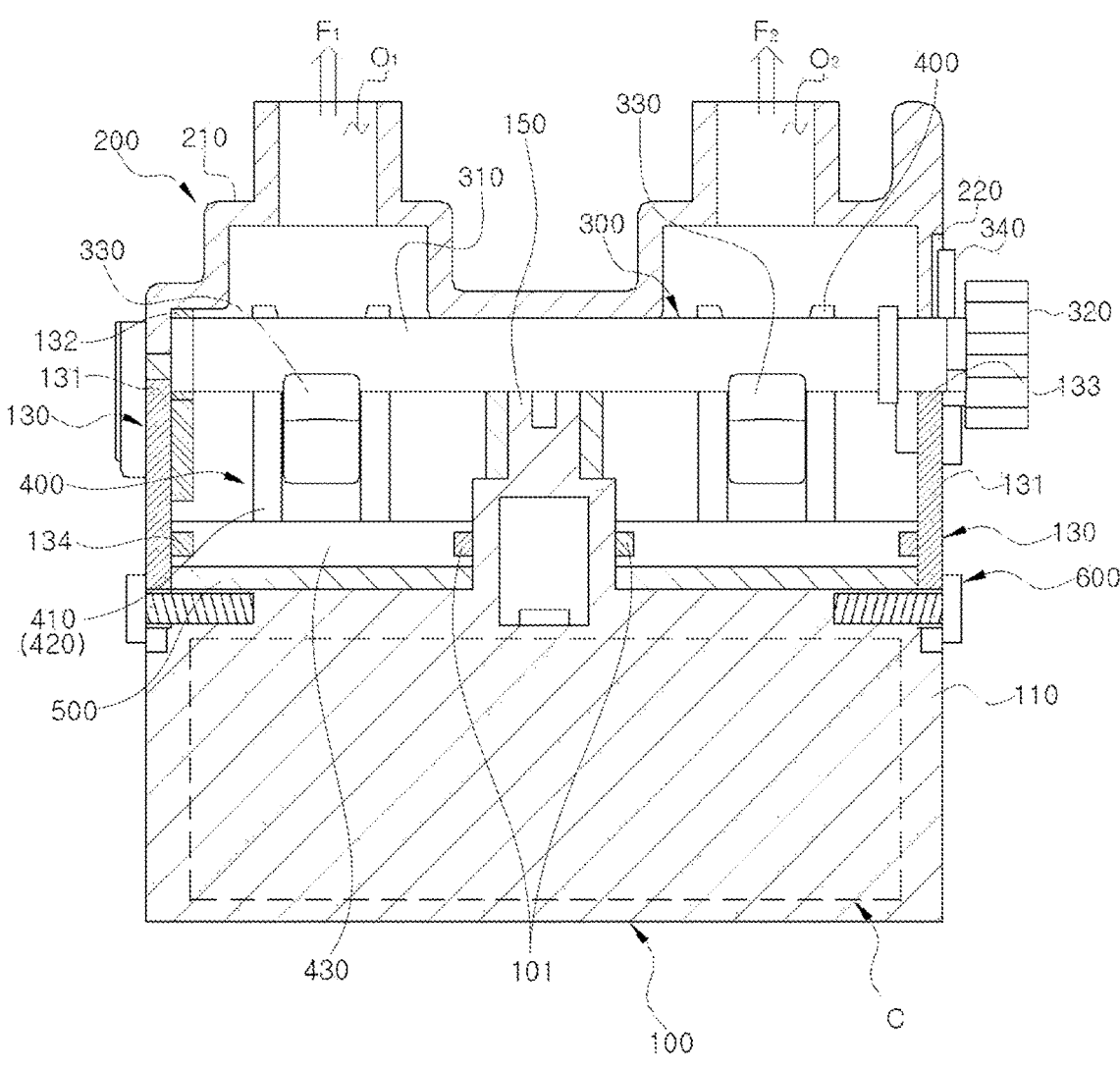
FIG. 4 is a cross-sectional front view of the fragrance generator for a vehicle according to the present invention.

FIGS. 3 and 4 relate to the fragrance generator for a vehicle according to the present invention. FIG. 3 is an exploded perspective view of the fragrance generator for a vehicle, and FIG. 4 is a cross-sectional front view taken along line A-A' in FIG. 2 and illustrating the fragrance generator for a vehicle.

With reference to FIG. 3, the fragrance generator 10 for a vehicle according to the present invention may include the housing part 100, the cover casing 200, a rotary member 300, an opening/closing member 400, or a sealing member 500. In this case, the fragrance generator 10 for a vehicle may be connected to the actuator 20, such that power may be applied to the rotary member 300. The housing part 100 or the cover casing 200 may be coupled to the actuator 20.

The housing part 100 may include a storage casing 110, a discharge port 120, a lateral casing 130, or a coupling guide 140. In this case, the storage casing 110 may have a hollow portion therein. The cartridge may be accommodated in a lower portion of the storage casing 110, and the fragrance may be discharged through the discharge port 120. Further, the discharge port 120 may be provided as a pair of discharge ports 120 including a first discharge port 121 and a second discharge port 122. Different fragrances may be discharged from the first discharge port 121 and the second discharge port 122. Further, the discharge port 120 may be provided as a plurality of discharge ports 120 in the leftward/ rightward direction, and the first discharge port 121 and the second discharge port 122 may also be provided as a plurality of first discharge ports 121 and a plurality of second discharge ports 122 in the leftward/rightward direction. The lateral casing 130 may be separably coupled to the storage casing 110. The lateral casing 130 may be provided as a pair of lateral casings 130 respectively disposed on left and right surfaces of the storage casing 110.

The cover casing 200 may be disposed above the storage casing 110. As described above, gas discharged from the discharge port 120 of the housing part 100 may be discharged to the outside through the cover casing 200. In this case, the cover casing 200 may include a cover body 210, a rotation stopper 220, a first coupling part 230, or a second coupling part 240. In this case, the cover body 210 may be coupled to an upper side of the storage casing 110 and seal an upper surface of the storage casing 110. Further, the first coupling part 230 may fix and couple the cover casing 200 and the housing part 100, and the second coupling part 240 may fix and couple the cover casing 200 and the actuator 20.

The rotary member 300 may be interposed between the cover body 210 and the storage casing 110. The rotary member 300 may be rotatably coupled to a lower side of the cover body 210 or an upper side of the storage casing 110. Further, the rotary member 300 may include a shaft body 310, a power application part 320, or an opening/closing adjustment part 330. In this case, the shaft body 310 may extend leftward and rightward and coupled to the cover body 210 or the storage casing 110. The power application part 320 may be connected to an end of the shaft body 310 and receive power from the actuator 20. In this case, the present invention will be described in more detail with reference to an example in which the actuator 20 is disposed on a right surface of the housing part 100. When the power application part 320 connected to a right end of the shaft body 310 is rotated by the actuator 20, the shaft body 310 may also be rotated. Further, one or more opening/closing adjustment parts 330 may be disposed on the shaft body 310, and the opening/closing adjustment part 330 may also be rotated together with the shaft body 310. In this case, the opening/closing adjustment part 330 may have a shape extending downward from an outer surface of the shaft body 310 and control a posture of the opening/closing member 400.

The opening/closing member 400 may include a first opening/closing part 410, a second opening/closing part 420, a rotary shaft 430, or a spring 440. In this case, the first opening/closing part 410 and the second opening/closing part 420 are configured to rotate within a predetermined angle about the rotary shaft 430. The first opening/closing part 410 may open or close an inlet of the first discharge port 121, and the second opening/closing part 420 may open or close an inlet of the second discharge port 122. Further, the spring 440 may be connected between the first opening/closing part 410 and the second opening/closing part 420 and maintain a constant interval between the first opening/closing part 410 and the second opening/closing part 420. In this case, when the opening/closing adjustment part 330 rotates together with the shaft body 310, a rotational force may be transmitted to the first opening/closing part 410 or the second opening/closing part 420. In case that the rotational force is applied to the first opening/closing part 410, the inlet of the first discharge port 121 may be closed, and the inlet of the second opening/closing part 420 may be opened. That is, power applied to the first opening/closing part 410 may move the second opening/closing part 420 by means of the spring 440. The rotary shafts 430 may be respectively provided for the first opening/closing part 410 and the second opening/closing part 420. Alternatively, the first opening/closing part 410 and the second opening/closing part 420 may be rotated about the same rotary shaft 430.

The sealing member 500 may include an elastic body 510, flow holes 520, or a groove 530. The elastic body 510 may be made of an elastic material and interposed between the storage casing 110 and the cover casing 200. The opening/closing member 400 may be seated on an upper surface of the elastic body 510. Further, the plurality of flow holes 520 may be formed through the elastic body 510, and the plurality of flow holes 520 may communicate with the plurality of discharge ports 120. Further the groove 530 is a groove recessed and extending leftward and rightward. The rotary shaft 430 of the opening/closing member 400 may be seated in the groove 530.

With reference to FIG. 4, the lateral casing 130 may be provided as a pair of lateral casings 130. The pair of lateral casings 130 may be respectively coupled to left and right surfaces of the storage casing 110. Further, one lateral casing 130 disposed on the left surface may include a lateral body 131 fixed to the left surface of the storage casing 110, and a shaft support part 132 into which a left end of the shaft body 310 is inserted. The other lateral casing 130 disposed on the right surface may include a lateral body 131 fixed to the right surface of the storage casing 110, and a shaft seating part 133 configured to support a lower side of the right end of the shaft body 310. Further, the pair of lateral casings 130 and the storage casing 110 are screw-coupled by means of fastening member 600, such that the pair of lateral casings 130 and the storage casing 110 are easily separated and coupled. The pair of lateral casings 130 and the storage casing 110 may be integrated by other means such as a bonding agent or welding.

The rotary member 300 may further include a rotation adjustment part 340 disposed at the right end of the shaft body 310 and extending upward. Further, the rotation adjustment part 340 may move on the rotation stopper 220 disposed on the right surface of the cover body 210. The rotation stopper 220 may limit a rotation angle of the rotation adjustment part 340 to a predetermined angle or less. Therefore, a rotation angle of the shaft body 310 is also limited. A rotation angle of the one or more opening/closing adjustment parts 330 disposed on the shaft body 310 may also be limited to a predetermined angle or less.

The housing part 100 may further include a partition part 150 configured to partition an upper portion of the storage casing 110 in the leftward/rightward direction. In this case, when an upper hollow portion of the storage casing 110 is partitioned into a plurality of portions, the opening/closing adjustment part 330 and the opening/closing member 400 may be provided as a plurality of opening/closing adjustment parts 330 and a plurality of opening/closing members 400. The plurality of opening/closing adjustment parts 330 and the plurality of opening/closing members 400 may be disposed to be spaced apart from one another leftward and rightward. Further, the fragrance discharged from a cartridge part C accommodated at a lower side of the storage casing 110 may flow to the cover casing 200 along the partitioned upper hollow portions of the storage casing 110. Further, the upper side of the cover body 210 of the cover casing 200 includes the plurality of discharge ports O including the first discharge port $O_1$ and the second discharge port $O_2$, such that the plurality of fluids $F_1$ and $F_2$ may be discharged to the outside.

Figure 5:
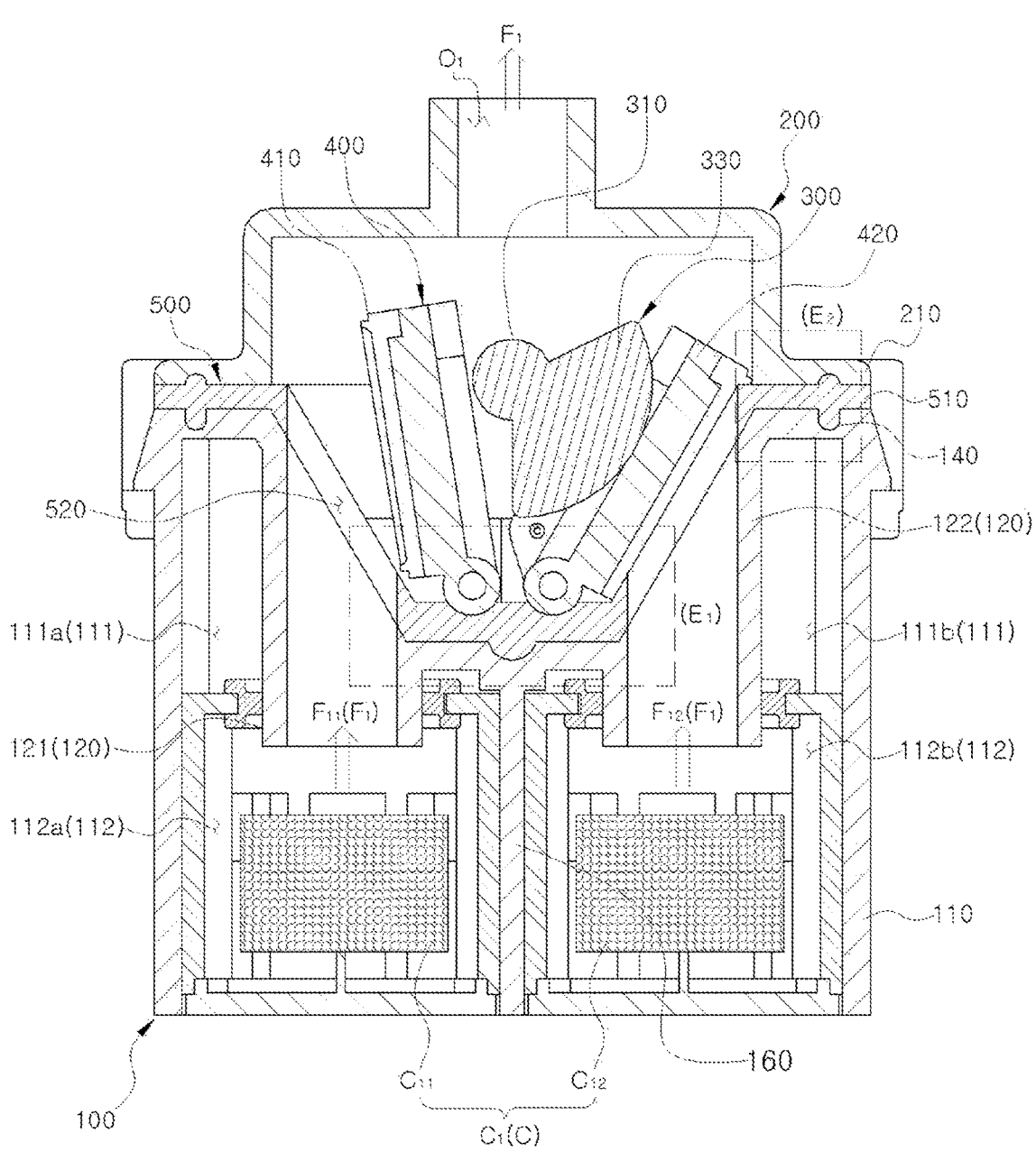
FIG. 5 is a cross-sectional side view of the fragrance generator for a vehicle according to the present invention.
Figure 6:
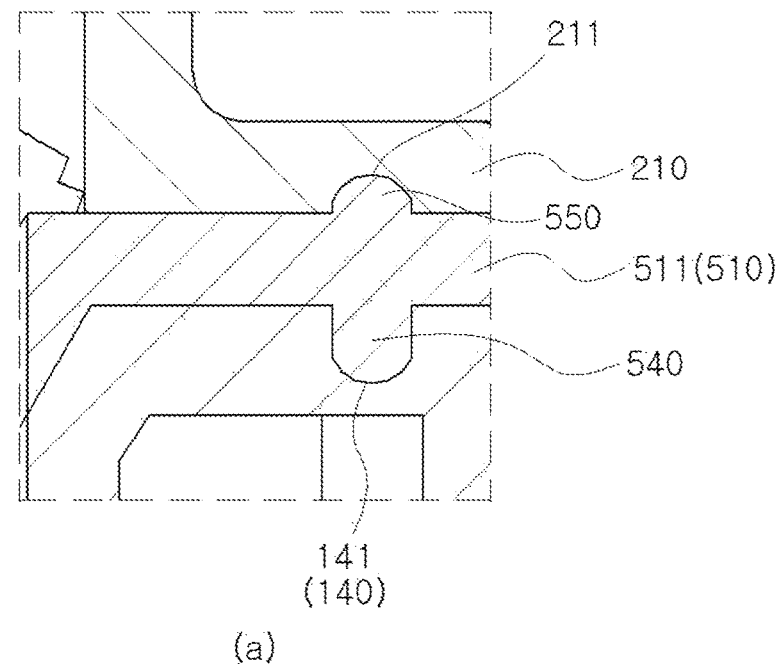
FIG. 6 is a partially enlarged cross-sectional side view of the fragrance generator for a vehicle according to the present invention.
Figure 6:
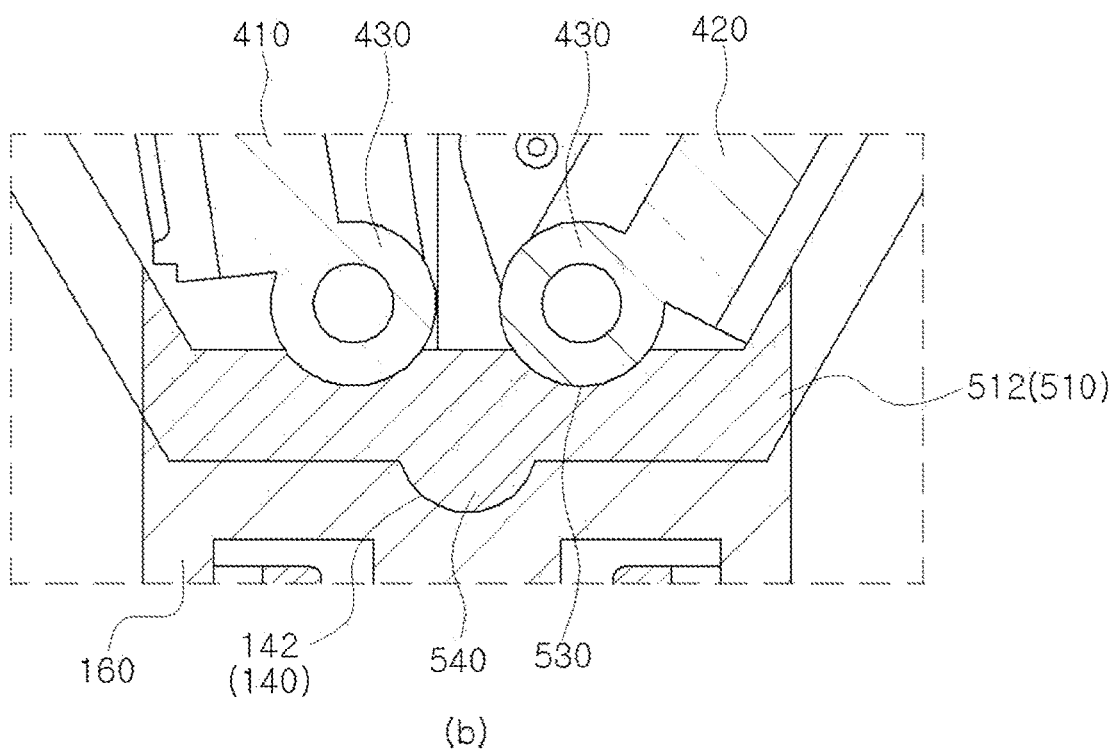

FIGS. 5 and 6 relate to the fragrance generator for a vehicle according to the present invention. FIG. 5 is a cross-sectional side view taken along line B-B' in FIG. 2 and illustrating the fragrance generator for a vehicle, and FIG. 6 is an enlarged view of $E_1$ and $E_2$ in FIG. 5.

With reference to FIG. 5, the cartridge part C may include a plurality of fragrance cartridges $C_1$ in the leftward/rightward direction. The fragrance cartridges $C_1$ may also include a first fragrance cartridge $C_{11}$ and a second fragrance cartridge $C_{12}$ spaced apart from each other in the forward/rearward direction (the leftward/rightward direction in the drawing). Further, the first fluid $F_1$ generated in the first fragrance cartridge $C_{11}$ or the second fragrance cartridge $C_{12}$ may be discharged to the outside through the first discharge port $O_1$. The opening/closing member 400 may adjust the fluid to be discharged by opening or closing the first discharge port 121 connected to the first fragrance cartridge $C_{11}$ or the second discharge port 122 connected to the second fragrance cartridge $C_{12}$. In this case, the discharged fluid may be a single fragrance or a mixture of fragrances.

The housing part 100 may further include a partition wall part 160 to divide the interior of the storage casing 110 in the forward/rearward direction. A first hollow portion 111, which is an upper hollow portion of the storage casing 110, may be divided into a first-first hollow portion 111*a* and a first-second hollow portion 111*b* in the forward/rearward direction. A second hollow portion 112, which is a lower hollow portion of the storage casing 110, may be divided into a second-first hollow portion 112*a* and a second-second hollow portion 112*b* in the forward/rearward direction. Further, the first fragrance cartridge $C_{11}$ may be disposed in the second-first hollow portion 112*a* and discharge a first-first fluid $F_{11}$ to the cover casing 200 through the first discharge port 121 disposed in the first-first hollow portion 111*a*. The second fragrance cartridge $C_{12}$ may be disposed in the second-second hollow portion 112*b* and discharge a first-second fluid $F_{12}$ to the cover casing 200 through the second discharge port 122 disposed in the first-second hollow portion 111*b*.

Front and rear ends of the elastic body 510 of the sealing member 500 may be seated on the upper surface of the storage casing 110, and a central portion of the elastic body 510 based on the forward/rearward direction may be seated on the upper surface of the partition wall part 160. Further, the pair of flow holes 520 may be disposed between the ends of the elastic body 510 based on the forward/rearward direction and the central portion of the elastic body 510 and communicate with the first discharge port 121 and the second discharge port 122.

As illustrated in FIG. 6, the coupling guide 140 may include a first coupling guide 141 or a second coupling guide 142. In this case, as illustrated in FIG. 6A, the first coupling guide 141 may be disposed on an upper surface of a front side or a rear side of the storage casing 110 and guide a position of an end 511 of the elastic body 510 based on the forward/rearward direction. For example, the first coupling guide 141 is provided in the form of a groove. The end 511 of the elastic body 510 based on the forward/rearward direction may include a seating portion 540 protruding downward, such that the coupling may be guided. The first coupling guide 141 may be provided in the form of a protrusion, and the seating portion 540 may be provided in the form of a groove. Further, insertion portions 211 and 550 may be respectively formed in a lower surface of the cover body 210 and an upper surface of the elastic body 510. One of the insertion portion 211 of the cover body 210 and the insertion portion 550 of the elastic body 510 may be provided in the form of a groove, and the other of the insertion portion 211 of the cover body 210 and the insertion portion 550 of the elastic body 510 may be provided in the form of a protrusion corresponding in shape to the groove.

Next, as illustrated in FIG. 6B, the second coupling guide 142 may be disposed on the upper surface of the partition wall part 160 of the storage casing 110 and guide a position of a central portion 512 of the elastic body 510 based on the forward/rearward direction. For example, the second coupling guide 142 is provided in the form of a groove. The central portion 512 of the elastic body 510 based on the forward/rearward direction may include the seating portion 540 protruding downward, such that the coupling may be guided. The first coupling guide 141 may be provided in the form of a protrusion, and the seating portion 540 may be provided in the form of a groove. Further, the groove 530 is recessed in an upper surface of the central portion 512 of the elastic body 510 based on the forward/rearward direction. A lower portion of the rotary shaft 430, which is a rotation center of the first opening/closing part 410 or the second opening/closing part 420, may be inserted into the groove 530.

Figure 7:
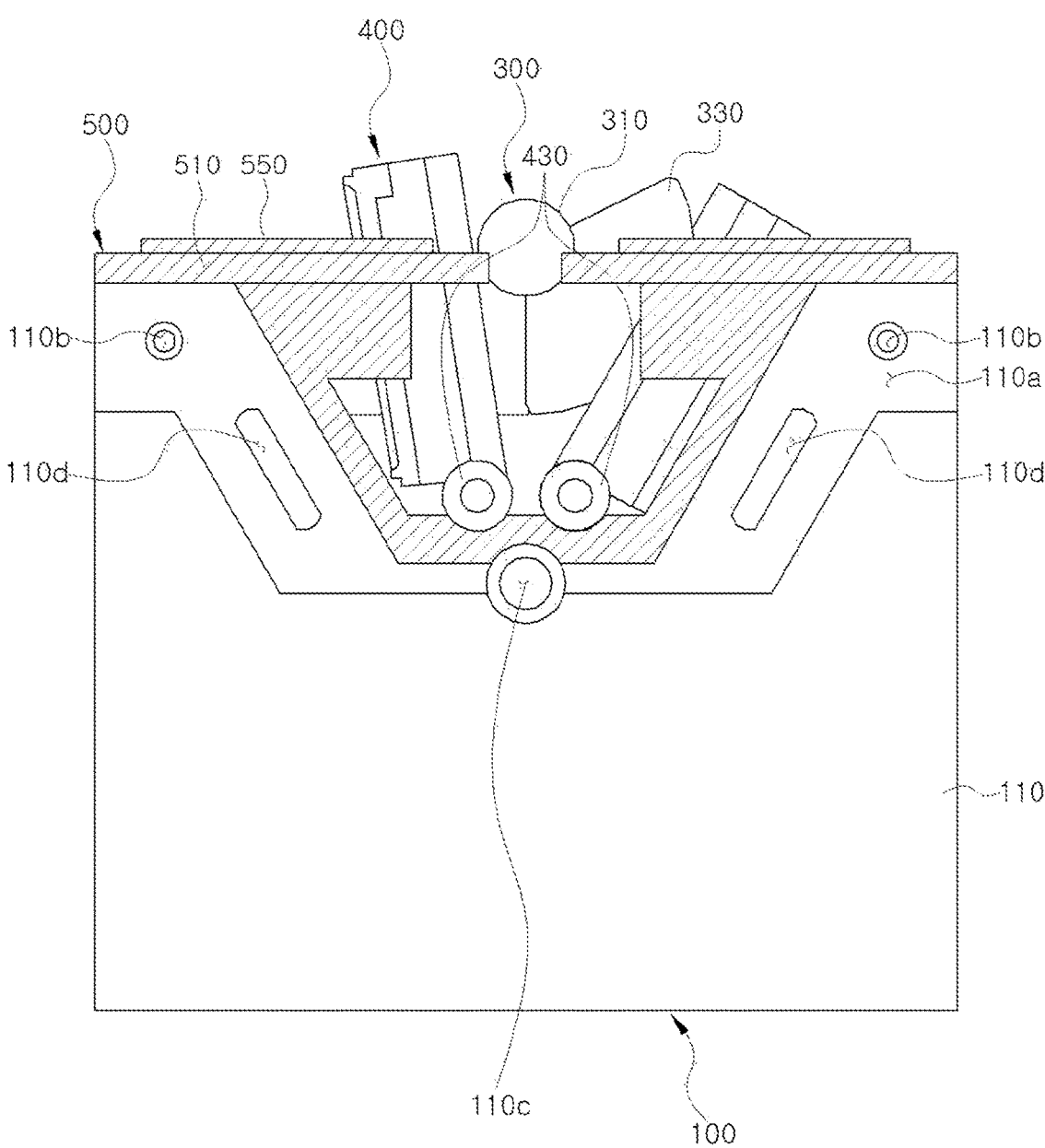
FIG. 7 is a side view illustrating a storage casing from which a cover casing and a lateral casing according to the present invention are separated.
Figure 8:
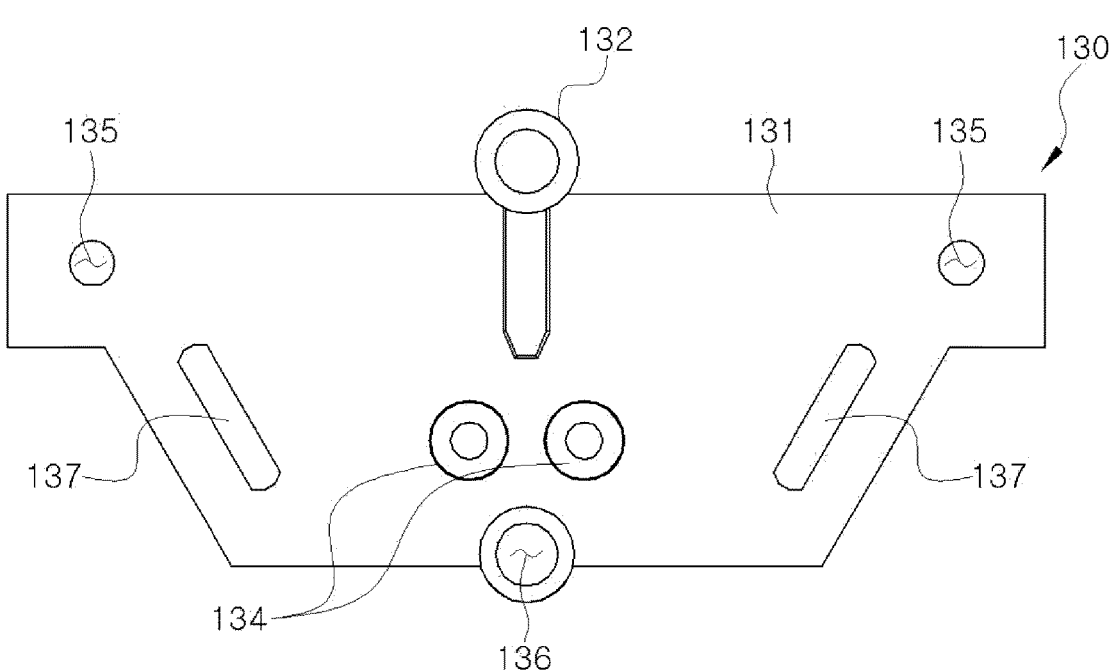
FIG. 8 is a right side view of a first cover casing according to the present invention.
Figure 9:
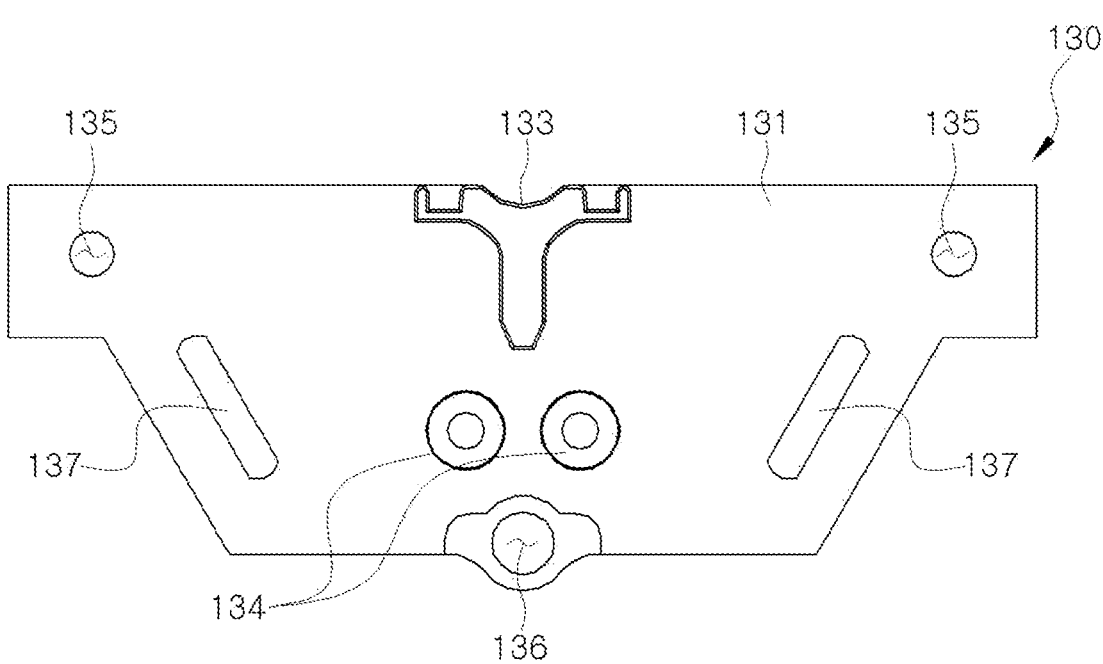
FIG. 9 is a left side view of a second cover casing according to the present invention.

FIGS. 7 to 9 relate to the fragrance generator for a vehicle according to the present invention. FIG. 7 is a side view of the storage casing from which the cover casing and the lateral casing are separated, FIG. 8 is a right side view of the first cover casing, and FIG. 9 is a left side view of the second cover casing.

With reference to FIG. 7, a mounting groove 110a may be recessed in an upper surface of the storage casing 110, and the lateral casing 130 may be coupled to the mounting groove 110a. Further, the storage casing 110 may further include a coupling hole 110b, a fixing hole 110c, or an insertion guide 110d disposed in the mounting groove 110a. Further, the coupling hole 110b and the fixing hole 110c may have screw threads formed therein so as to be screw-coupled, and the insertion guide 110d may have a groove or protrusion shape. Further, the rotary shaft 430 of the opening/closing member 400 may have a shape protruding in a transverse direction. Hereinafter, FIGS. 8 and 9 will be described with reference to the shape in FIG. 7.

As illustrated in FIG. 8, one lateral casing 130 may include the lateral body 131, the shaft support part 132, end support parts 134, first communication holes 135, a second communication hole 136, or insertion guides 137 so as to be mounted on an upper left surface of the storage casing 110. In this case, the lateral body 131 may correspond in shape to the mounting groove 110a of the storage casing 110 and be formed to seal the elastic body 510 of the sealing member 500 disposed at the upper side of the storage casing 110. Further, the shaft support part 132 may have a groove corresponding in shape to a left end of the shaft body 310 so that the left end of the shaft body 310 of the rotary member 300, which controls the opening/closing member 400, may be inserted into the groove. Further, the end of the rotary shaft 430 may be inserted into the end support part 134. In case that the rotary shaft 430 may be provided as a pair of rotary shafts 430 that serves as rotation centers of the first opening/closing part 410 and the second opening/closing part 420, the end support part 134 may also be provided as a pair of end support parts 134, and the pair of rotary shafts 430 may be respectively inserted into the pair of end support parts 134. In this case, the shaft body 310 and the rotary shaft 430 may be rotatably connected to the shaft support part 132 and the end support part 134. The first communication hole 135 and the second communication hole 136 may communicate with each other in the leftward/rightward direction so that the fastening member 600 may be inserted. The first communication hole 135 and the coupling hole 110b may be disposed at an end based on the forward/rearward direction, and the second communication hole 136 and the fixing hole 110c may be disposed at a central portion based on the forward/rearward direction. Further, the second communication hole 136 may be disposed below the end support part 134.

As illustrated in FIG. 9, the other lateral casing 130 may also include the lateral body 131, the shaft seating part 133, the end support parts 134, the first communication holes 135, the second communication hole 136, or the insertion guides 137 so as to be mounted on an upper right surface of the storage casing 110. In this case, the shaft seating part 133 may be disposed to support a lower surface of a right end of the shaft body 310 and recessed in a shape corresponding to a lower portion of a rear side of the shaft body 310.

This configuration will be described more clearly with reference to FIG. 4. Two opposite ends of the rotary shaft 430 of the opening/closing member 400 may be fixed to the end support parts 134 of the pair of lateral casings 130. One end of the rotary shaft 430 may be fixed to the end support part 134 of one lateral casing 130, and the other end of the rotary shaft 430 may be fixed by an end support part 101 disposed in the storage casing 110. In this case, as illustrated, the end support part 101 disposed in the storage casing 110 may be disposed on the partition part 150. Although not illustrated, it is possible to implement various arrangement structures such as a structure in which the end support part 101 is disposed on an inner surface of the storage casing 110. The end support part 134 of the lateral casing 130, which is formed as described above, or the end support part 101, which is disposed in the storage casing 110, may protrude and be inserted and coupled into the groove of the rotary shaft 430 or may be provided in the form of a groove that may accommodate the rotary shaft 430. Further, when the position of the rotary shaft 430 is fixed by the end support part 134 of the lateral casing 130 or the end support part 101 disposed in the storage casing 110, the rotary shaft 430 may rotate at the fixed position and determine whether to open or close the flow hole 520 included in the sealing member 500. Further, as the fixed rotary shaft 430 presses the sealing member 500 downward, the housing part 100 and the sealing member 500 come into close contact with each other, which implements an advantage of further improving sealing performance. Further, the end support part 101 disposed in the storage casing 110 may further include a function of fixing the sealing member 500. Furthermore, when the end support part 134 of the lateral casing 130 or the end support part 101 disposed in the storage casing 110 protrudes, an effect of preventing the separation of the sealing member 500 disposed below the end support part is also implemented, thereby providing an advantage of improving durability.

Figure 10:
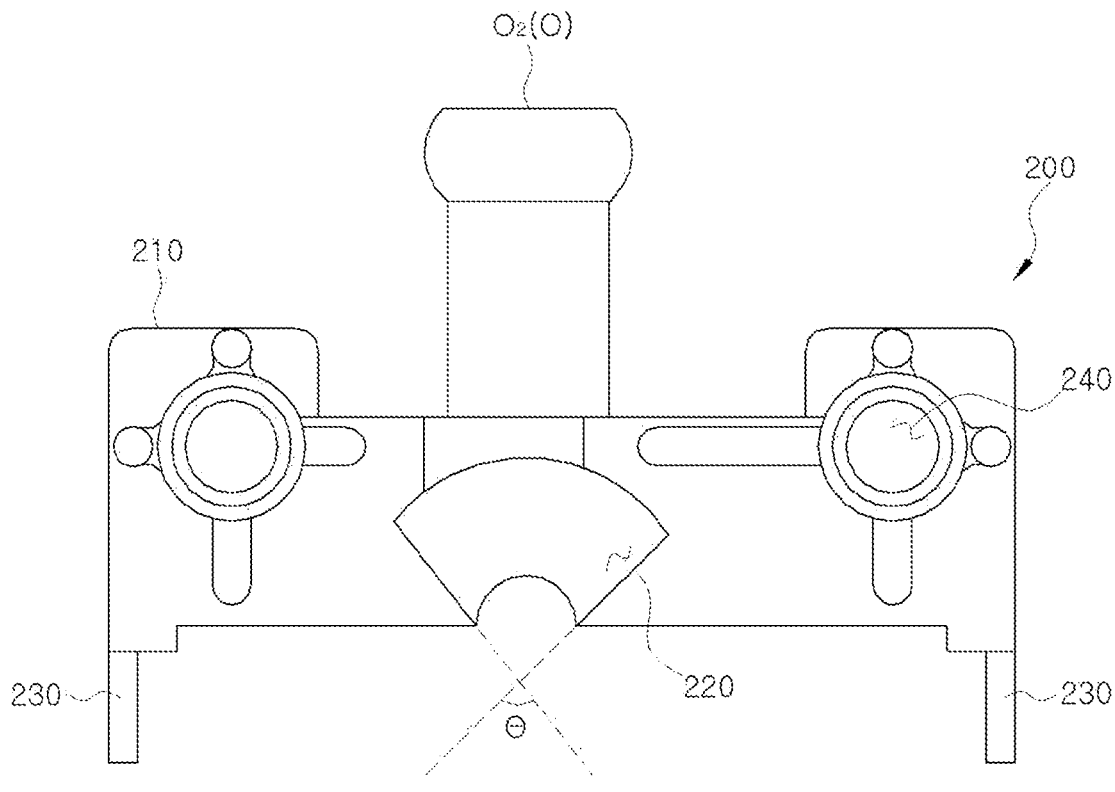
FIG. 10 is a right side view of the cover casing from which a rotary member according to the present invention is separated.
Figure 11:
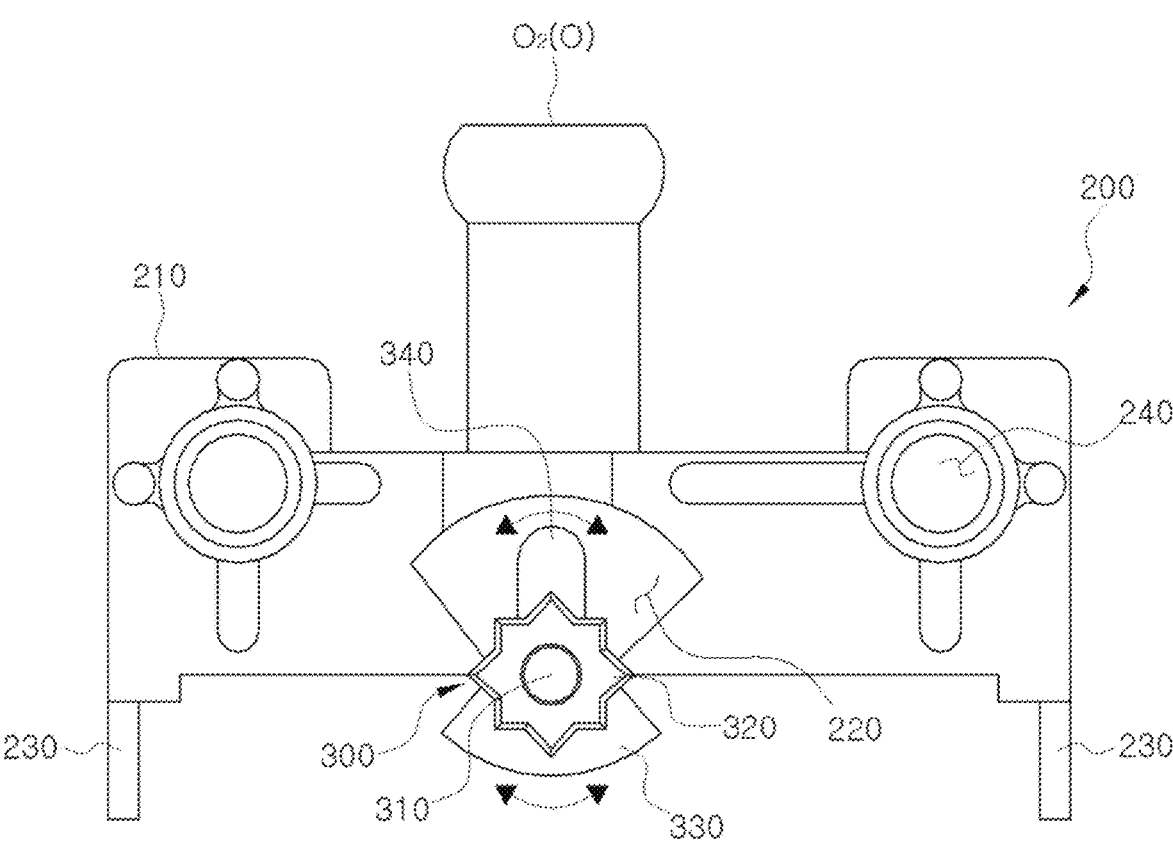
FIG. 11 is a right side view of the cover casing to which the rotary member according to the present invention is coupled.

FIGS. 10 and 11 relate to the fragrance generator for a vehicle according to the present invention. FIG. 10 is a right side view of the cover casing from which the rotary member inspected, and FIG. 11 is a right side view of the cover casing to which the rotary member is coupled.

With reference to FIGS. 10 and 11, as described above, the cover casing 200 may include the cover body 210, the rotation stopper 220, the first coupling part 230, or the second coupling part 240. The rotation stopper 220 may be disposed on the right surface of the cover body 210. Further, the rotary member 300 may include the shaft body 310, the power application part 320, the opening/closing adjustment part 330, or the rotation adjustment part 340. When power is applied to the power application part 320 from the actuator 20, the shaft body 310, the opening/closing adjustment part 330, and the rotation adjustment part 340 may rotate together. In this case, the rotation adjustment part 340 may have a shape protruding upward from the upper surface of the shaft body 310 and be disposed on the rotation stopper 220. Further, the rotation stopper 220 may be recessed, and a portion of the rotation stopper 220 based on the forward/ rearward direction protrudes rightward. The rotation adjustment part 340 reciprocates in the rotation stopper 220, such that the rotation adjustment part 340 may be adjusted to be rotated within a predetermined angle θ.

The present invention is not limited to the above embodiments, and the scope of application is diverse. Of course, various modifications and implementations made by any person skilled in the art to which the present invention pertains without departing from the subject matter of the present invention claimed in the claims.

DESCRIPTION OF REFERENCE NUMERALS

C: Cartridge part
$C_1$: Fragrance cartridge
$C_{11}$: First fragrance cartridge
$C_{12}$: Second fragrance cartridge
O: Discharge port
$O_1$: First discharge port
$O_2$: Second discharge port
10: Fragrance generator for vehicle
20: Actuator
100: Housing part
101: End support part
110: Storage casing
110*a*: Mounting groove
110*b*: Coupling hole
110*c*: Fixing hole
110*d*: Insertion guide
111: First hollow portion
111*a*: First-first hollow portion
111*b*: First-second hollow portion
112: Second hollow portion
112*a*: Second-first hollow portion
112*b*: Second-second hollow portion
120: Discharge port
121: First discharge port
122: Second discharge port
130: Lateral casing
131: Lateral body
132: Shaft support part
133: Shaft seating part
134: End support part
135: First communication hole
136: Second communication hole
137: Insertion guide
140: Coupling guide
141: First coupling guide
142: Second coupling guide
150: Partition part
160: Partition wall part
200: Cover casing
210: Cover body
211: Insertion portion
220: Rotation stopper
230: First coupling part
240: Second coupling part
300: Rotary member
310: Shaft body
320: Power application part
330: Opening/closing adjustment part
340: Rotation adjustment part 400: Opening/closing member
410: First opening/closing part
420: Second opening/closing part
430: Rotary shaft
440: Spring
500: Sealing member
510: Elastic body
520: Flow hole
530: Groove
540: Seating portion
550: Insertion portion
600: Fastening member

The invention claimed is:

1. A fragrance generator for a vehicle, the fragrance generator comprising:
   a storage casing configured to accommodate a plurality of fragrance cartridges therein;
   a cover casing coupled to one surface of the storage casing and configured to discharge a fragrance discharged from the fragrance cartridge;
   a rotary member interposed between the storage casing and the cover casing and having a length extending in one direction of one surface; and
   an opening/closing member having first and second opening/closing parts that rotate about a rotary shaft and adjust the fragrance discharged from a pair of fragrance cartridges,
   wherein when the rotary member rotates, the fragrance is discharged from one or more fragrance cartridges among the plurality of fragrance cartridges and discharged through the cover casing,
   wherein one or both of a pair of lateral casings disposed on two opposite surfaces of the storage casing is separably coupled to the storage casing,
   wherein the rotary member comprises a shaft body disposed on one surface of the storage casing and extending to two opposite sides,
   wherein one or both of the pair of lateral casings comprises a shaft support part into which the other end of the shaft body is inserted, and the other lateral casing comprises a shaft seating part on which one end of the shaft body is seated,
   wherein an end support part is configured to fix an end of the rotary shaft of the opening/closing member, wherein the end support part is disposed in the lateral casing or the storage casing,
   wherein the end support part, which is disposed in the storage casing, protrudes and is inserted and coupled into a groove formed at an end of the rotary shaft, and
   wherein the shaft support part has a groove corresponding in shape to the other end of the shaft body so that the other end of the shaft body of the rotary member, which controls the opening/closing member, is configured to be inserted into the groove.

2. The fragrance generator of claim 1, further comprising:
   first and second discharge ports disposed in the storage casing and respectively connected to a pair of fragrance cartridges; and
   an opening/closing member configured to open or close the first and second discharge ports,
   wherein at least one of the pair of lateral casings fixes a part of the opening/closing member.

3. The fragrance generator of claim 2, wherein the opening/closing member comprises:

first and second opening/closing parts configured to respectively open or close the first and second discharge ports while rotating within a predetermined angle; and a rotary shaft connected to the first and second opening/closing parts, and wherein the lateral casing fixes an end of the rotary shaft.

4. The fragrance generator of claim 1, wherein the rotary member comprises:

a power application part configured to transmit power, which is applied from an actuator, to one end of the shaft body; and an opening/closing adjustment part disposed on the shaft body and configured to control a posture of the opening/closing member.

5. The fragrance generator of claim 1, wherein the cover casing comprises:

a cover body having a discharge port through which the fragrance is discharged; and a rotation stopper disposed on one side surface of the cover body, wherein the rotary member comprises:

a shaft body having a length extending to two opposite sides; and a rotation adjustment part protruding from one side of the shaft body toward the cover casing and disposed on the rotation stopper, and wherein the shaft body rotates within a predetermined angle.

6. The fragrance generator of claim 1, further comprising:

a sealing member interposed between the storage casing and the cover casing, wherein a coupling guide is provided on a surface, on which the storage casing and the sealing member adjoin each other, to fix a coupling position of the sealing member.

7. The fragrance generator of claim 6, further comprising:

a partition wall part disposed in the storage casing and configured to divide and partition an interior of the storage casing, wherein the partition wall part and the sealing member are in surface contact with each other, and wherein a coupling guide is provided on a surface, on which the partition wall part and the sealing member adjoin each other, to fix a coupling position of the sealing member.

8. The fragrance generator of claim 6, further comprising:

an opening/closing member having first and second opening/closing parts that rotate about a rotary shaft and adjust the fragrance discharged from a pair of fragrance cartridges, wherein the sealing member has a groove in which a part of the rotary shaft is seated.

9. The fragrance generator of claim 6, wherein the cover casing and the sealing member have insertion portions formed in surfaces of the cover casing and the sealing member that adjoin each other, such that the cover casing and the sealing member are inserted and coupled into each other.

10. The fragrance generator of claim 1, wherein the lateral casing comprises:

a lateral body; and a communication hole formed through the lateral body, and wherein a fastening member penetrates the communication hole and is coupled to the storage casing.

11. The fragrance generator of claim 10, wherein a mounting groove is recessed in one surface of the storage casing so that the lateral body is inserted into the mounting groove.

12. The fragrance generator of claim 1, wherein the lateral casing comprises:

a lateral body; and an insertion guide configured to guide coupling positions of the lateral body and one surface of the storage casing.

13. The fragrance generator of claim 12, wherein a mounting groove is recessed in one surface of the storage casing so that the lateral body is inserted into the mounting groove.

14. The fragrance generator of claim 1, further comprising:

a sealing member interposed between the storage casing and the cover casing, wherein a part of the sealing member is disposed in the storage casing so that the rotary shaft of the opening/closing member is seated on the sealing member, and wherein the rotary shaft fixed by the end support part presses one surface of the opening/closing member so that the other surface of the opening/closing member is in close contact with the sealing member in a direction in which the storage casing is disposed.

* * * * *